United States Patent
Ishii et al.

(10) Patent No.: US 9,024,075 B2
(45) Date of Patent: May 5, 2015

(54) PROCESS FOR PRODUCING α-FLUOROALDEHYDES

(75) Inventors: Akihiro Ishii, Kawagoe (JP); Takashi Ootsuka, Kawagoe (JP); Mari Imamura, Kawagoe (JP); Takayuki Nishimiya, Kawagoe (JP); Kazuto Kimura, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/233,629

(22) PCT Filed: Jul. 24, 2012

(86) PCT No.: PCT/JP2012/068639
§ 371 (c)(1),
(2), (4) Date: Jan. 17, 2014

(87) PCT Pub. No.: WO2013/018573
PCT Pub. Date: Feb. 7, 2013

(65) Prior Publication Data
US 2014/0194654 A1  Jul. 10, 2014

(30) Foreign Application Priority Data

Aug. 3, 2011 (JP) ................... 2011-170194
Feb. 28, 2012 (JP) ................... 2012-041213
Jul. 9, 2012 (JP) ................... 2012-153460

(51) Int. Cl.
*C07C 45/41* (2006.01)
*C07C 41/50* (2006.01)

(52) U.S. Cl.
CPC ............ *C07C 45/41* (2013.01); *C07C 41/50* (2013.01)

(58) Field of Classification Search
USPC ........................................................ 568/484
See application file for complete search history.

(56) References Cited

U.S. PATENT DOCUMENTS

| | | | |
|---|---|---|---|
| 5,248,832 A | 9/1993 | Lee | |
| 5,334,769 A | 8/1994 | Ferrero et al. | |
| 5,476,827 A | 12/1995 | Ferrero et al. | |
| 5,679,869 A | 10/1997 | Schnurr et al. | |
| 6,180,830 B1 | 1/2001 | Jacquot | |
| 8,471,048 B2 | 6/2013 | Kuriyama et al. | |
| 2011/0237814 A1 | 9/2011 | Kuriyama et al. | |
| 2013/0303774 A1 | 11/2013 | Ishii et al. | |

FOREIGN PATENT DOCUMENTS

| | | |
|---|---|---|
| JP | 5-170693 A | 7/1993 |
| JP | 5-294882 A | 11/1993 |
| JP | 8-231458 A | 9/1996 |
| JP | 11-501575 A | 2/1999 |
| WO | WO 97/17134 | 5/1997 |
| WO | WO 2011/048727 A1 | 4/2011 |
| WO | WO 2012/105431 A1 | 8/2012 |

OTHER PUBLICATIONS

International Search Report (PCT/ISA/210), including English translation dated Nov. 6, 2012 (Five (5) pages).
Japanese langauge Written Opinion (PCT/ISA/237) dated Nov. 6, 2012 (Three (3) pages).
Noyori, et al. "Organic Chemistry for Graduate Students vol. II: Molecular Structure & Reaction/Organic Metal Chemistry", pp. 388-391, Tokyo Kagaku Dojin, 1999, including partial English translation (Five (5) pages).
L.S. Hegedus., "Transition Metals in the Synthesis of Complex Organic Molecules", Second Edition, pp. 4-9, Tokyo Kagaku Dojin, 2001, including partial English translation (Eight (8) pages).
Protective Groups in Organic Synthesis, Third Edition, 1999, John Wiley & Sons, Inc. (Twenty-eight (28) pages).
Journal of the American Chemical Society (U.S.), 1954, vol. 76, p. 300, (Two (2) pages).
Kagaku Daijiten (Tokyo Kagaku Dojin, edited by Michinori Ohki, et al.), including partial English translation (Four (4) pages), (1989).

*Primary Examiner* — Sikarl Witherspoon
(74) *Attorney, Agent, or Firm* — Crowell & Moring LLP

(57) ABSTRACT

A production process of an α-fluoroaldehyde according to the present invention includes reaction of an α-fluoroester with hydrogen gas ($H_2$) in the presence of a ruthenium complex. It is possible in the present invention to allow relatively easy industrial production of the α-fluoroaldehyde and to directly obtain, as stable synthetic equivalents of the α-fluoroaldehyde, not only a hydrate (as obtained by conventional techniques) but also a hemiacetal that is easy to purify and is of high value in synthetic applications. The present invention provides solutions to all problems in the conventional techniques and establishes the significantly useful process for production of the α-fluoroaldehyde.

7 Claims, No Drawings

PROCESS FOR PRODUCING α-FLUOROALDEHYDES

FIELD OF THE INVENTION

The present invention relates to a process for industrial production of α-fluoroaldehydes.

BACKGROUND ART

α-Fluoroaldehydes can be produced by reduction of corresponding α-fluoroesters. For such reduction reactions, it is often the case to use stoichiometric amounts of hydride reducing agents e.g. sodium borohydride, lithium aluminum hydride etc. (see Patent Document 1 and Non-Patent Document 1). However, the processes for production of α-fluoroaldehydes using the stoichiometric amounts of hydride reducing agents are not suitable for large-scale production applications in view of the facts that: the hydride reducing agents are expensive and need to be handled with great caution; and the post treatments of the resulting reaction products require complicated operations and cause large amounts of wastes.

On the other hand, there have been proposed, as relevant techniques, process for production of fluoral hydrates by reaction of trifluoroacetic acids (including corresponding esters) with hydrogen gas ($H_2$) in the presence of ruthenium/tin bimetal catalysts in vapor phases (see Patent Documents 2 and 3).

PRIOR ART DOCUMENTS

Patent Documents

Patent Document 1: Japanese Laid-Open Patent Publication No. H05-170693
Patent Document 2: Japanese Laid-Open Patent Publication No. H05-294882
Patent Document 3: International Publication No. WO 97/017134

Non-Patent Documents

Non-Patent Document 1: Journal of the American Chemical Society (U.S.), 1954, vol. 76, p. 300

SUMMARY OF THE INVENTION

Problems to be Solved by the Invention

The production process using the hydrogen gas in the presence of the bimetal catalysts provides solutions to all problems raised in the production process using the stoichiometric amount of hydride reducing agent, but lead to high industrial manufacturing cost due to the need for special production equipment to perform the reaction in the vapor phase under high-temperature conditions.

It is therefore an object of the present invention to provide a process for industrially producing an α-fluoroaldehyde by hydrogen reduction of an α-fluoroester without the need for special production equipment. As far as the present inventors know, there has been no specific report about the hydrogen reduction of α-fluoroesters and particularly about the production of α-fluoroaldehydes by hydrogen reduction of α-fluoroesters with the use of homogeneous catalysts. In the present specification, the term "homogeneous catalyst" is a catalyst as defined in Kagaku Daijiten (Tokyo Kagaku Dojin, edited by Michinori Ohki, Toshiaki Osawa, Motoharu Tanaka and Hideaki Chihara) and the like.

Means for Solving the Problems

As a result of extensive researches, the present inventors have found that a ruthenium complex of the following general formula [2], especially a ruthenium complex of the following general formula [4], can be used as a catalyst or precursor thereof for hydrogen reduction of an α-fluoroester without the need for special production equipment. This ruthenium complex functions as a homogeneous ruthenium catalyst, which is different from the supported-type (heterogeneous) ruthenium/tin bimetal catalysts of Patent Documents 2 and 3.

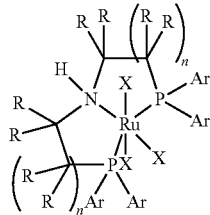

[2]

In the general formula [2], R each independently represents a hydrogen atom, an alkyl group, a substituted alkyl group, an aromatic ring group or a substituted aromatic ring group; Ar each independently represents an aromatic ring group or a substituted aromatic ring group; X each independently represents a ligand with a formal charge of −1 or 0 (with the proviso that the sum of the formal charges of three X is −2); and n each independently represents an integer of 1 or 2.

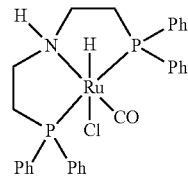

[4]

In the general formula [4], Ph each independently represent a phenyl group.

The present applicant has filed, as a technique relevant to the present invention, an application for a process for industrial production of a β-fluoroalcohol by reduction of an α-fluoroester with a dramatic reduction in hydrogen pressure (hereinafter referred to as "relevant application"). The disclosure of the relevant application is summarized as follows. In the relevant application, the β-fluoroalcohol is produced by reaction of the α-fluoroester of the general formula [1] with hydrogen gas in the presence of a specific ruthenium complex (as corresponding to the ruthenium complex of the following general formula [2], especially the ruthenium complex of the following general formula [4], of the present invention). In the production process of the relevant application, there is no need to use a high-pressure gas production facility as the hydrogen pressure can preferably be set to 1 MPa or lower. Further, the amount of the catalyst used can be reduced to a significantly low level (e.g. a substrate/catalyst ratio of 20,000) in the production process of the relevant application as compared to the substrate/catalyst ratio (e.g. 1,000) in the conventional reduction processes of α-fluoroalcohols. It is possible by these reductions in hydrogen pressure and catalyst amount to largely reduce the production cost of the β-fluoroalcohol. In addition, the reduction reaction is inert to unsaturated bonds (such as carbon-carbon double bond) in the production process of the relevant application so that it is a preferred embodiment of the relevant application to carry out the reduction reaction in a functional-group-selective manner (see Comparative Examples 1, 2, 3 and 4 as explained later in the present specification).

The α-fluoroester as the raw substrate material of the relevant application is represented by the following formula.

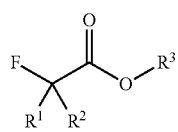

In the above formula, $R^1$ and $R^2$ each independently represent a hydrogen atom, a halogen atom, an alkyl group, a substituted alkyl group, an aromatic ring group or a substituted aromatic ring group; and $R^3$ represents an alkyl group or a substituted alkyl group.

Further, the β-fluoroalcohol as the target product of the relevant application is represented by the following formula.

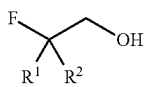

In the above formula, $R^1$ and $R^2$ have the same meanings as those of the α-fluoroester.

The present invention and the relevant application are similar to each other in that: the halogen atom used as $R^1$ and $R^2$ in the α-fluoroester of the relevant application can be the same as the halogen atom used as $R^1$ in the α-fluoroester of the general formula [1] of the present invention; the alkyl or substituted alkyl group used as $R^1$ and $R^2$ in the α-fluoroester of the relevant application can be the same as the alkyl or substituted alkyl group used as $R^2$ in the α-fluoroester of the general formula [1] of the present invention; the aromatic ring or substituted aromatic ring group used as $R^1$ and $R^2$ in the α-fluoroester of the relevant application can be the same as the aromatic ring or substituted aromatic ring group used as R in the ruthenium complex of the general formula [2] of the present invention; and the alkyl or substituted alkyl group used as $R^3$ in the α-fluoroester of the relevant application can be the same as the alkyl or substituted alkyl group used as $R^2$ in the α-fluoroester of the general formula [1] of the present invention.

The present invention is however clearly different from the relevant application in the kind of the raw substrate material. The raw material substrate of the present invention corresponds to those in which one of $R^1$ and $R^2$ of the α-fluoroester as the raw material of the relevant application is a fluorine atom and the other is a halogen atom or a haloalkyl group. It has been found that the α-fluoroaldehyde can be selectively obtained as a hydrogen reduction intermediate from the raw material substrate of the present invention. Although the raw substrate material of the present invention is included in the raw substrate material of the relevant application, not only the α-fluoroaldehyde but also a β-fluoroalcohol as a by-product are obtained in the present invention. There is thus no limitation imposed by the present invention on the relevant application. In the present invention, the by-produced β-fluoroalcohol can be easily separated by purification from the target α-fluoroaldehyde because of the large difference between the physical properties of the α-fluoroaldehyde and the β-fluoroalcohol. There is thus no limitation imposed by the relevant application onto the production process of the α-fluoroaldehyde according to the present invention.

In this way, the present inventors have found the useful techniques for industrial production of the α-fluoroaldehyde. The present invention is based on these findings.

The present invention thus provides a production process of an α-fluoroaldehyde as defined by the following aspects 1 to 9.

[Inventive Aspect 1]

A process for producing an α-fluoroaldehyde of the general formula [3], comprising: reaction of an α-fluoroester of the general formula [1] with hydrogen gas ($H_2$) in the presence of a ruthenium complex of the general formula [2]

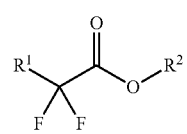

where $R^1$ represents a halogen atom or a haloalkyl group; and $R^2$ represents an alkyl group or a substituted alkyl group,

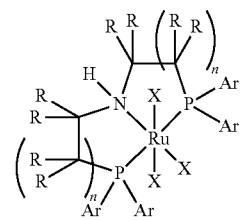

where R each independently represents a hydrogen atom, an alkyl group, a substituted alkyl group, an aromatic ring group or a substituted aromatic ring group; Ar each independently represents an aromatic ring group or a substituted aromatic ring group; X each independently represents a ligand with a formal charge of −1 or 0 (with the proviso that the sum of the formal charges of three X is −2); and n each independently represents an integer of 1 or 2,

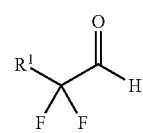

where $R^1$ has the same meaning as in the general formula [1].

[Inventive Aspect 2]

The process according to Inventive Aspect 1, wherein the reaction is performed in the presence of a base.

[Inventive Aspect 3]

A process for producing an α-fluoroaldehyde of the general formula [3], comprising: reaction of an α-fluoroester of the general formula [1] with hydrogen gas (H$_2$) in the presence of a ruthenium complex of the general formula [4]

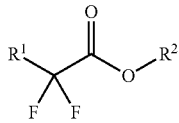

[1]

where R$^1$ represents a halogen atom or a haloalkyl group; and R$^2$ represents an alkyl group or a substituted alkyl group,

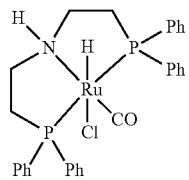

[4]

where Ph represents a phenyl group,

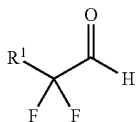

[3]

where R$^1$ has the same meaning as in the general formula [1].

[Inventive Aspect 4]

The process according to any one of Inventive Aspects 1 to 3, wherein the α-fluoroester of the general formula [1] is an α-fluoroester of the general formula [5]; and the α-fluoroaldehyde of the general formula [3] is an α-fluoroaldehyde of the general formula [6]

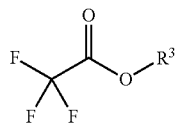

[5]

where R$^3$ is an alkyl group,

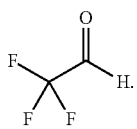

[6]

[Inventive Aspect 5]

The process according to any one of Inventive Aspects 1 to 4, wherein the reaction is performed at a hydrogen pressure of 2 MPa or lower.

[Inventive Aspect 6]

The process according to any one of Inventive Aspects 1 to 4, wherein the reaction is performed at a hydrogen pressure of 1 MPa or lower.

[Inventive Aspect 7]

The process according to any one of Inventive Aspects 1 to 4, wherein the reaction is performed at a hydrogen pressure of 0.5 MPa or lower.

[Inventive Aspect 8]

A process for producing an α-fluoroaldehyde of the general formula [3], comprising: reaction of an α-fluoroester of the general formula [1] with hydrogen gas (H$_2$) in the presence of a ruthenium catalyst

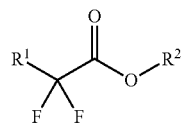

[1]

where R$^1$ represents a halogen atom or a haloalkyl group; and R$^2$ represents an alkyl group or a substituted alkyl group,

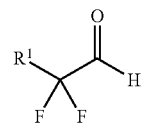

[3]

where R$^1$ has the same meaning as in the general formula [1].

[Inventive Aspect 9]

The process according to Inventive Aspect 8, wherein the ruthenium catalyst is a homogeneous catalyst.

In the present invention, there is no need to use special production equipment for hydrogen reduction of the α-fluoroester. There is also no need to use a high-pressure gas production facility by adoption of the preferable hydrogen pressure condition (1 MPa or lower) in the present invention. It is therefore possible to allow relatively easy industrial production of the α-fluoroaldehyde. Further, it is possible to directly obtain, as stable synthetic equivalents of the α-fluoroaldehyde (as explained later), not only a hydrate (as obtained by conventional techniques) but also a hemiacetal that is easy to purify and is of high value in synthetic applications.

As mentioned above, the present invention provides solutions to all problems in the conventional techniques and establishes the significantly useful process for production of the α-fluoroaldehyde.

DETAILED DESCRIPTION OF THE INVENTION

The production process of the α-fluoroaldehyde according to the present invention will be described below in detail. It should be noted that: the scope of the present invention is not limited to the following examples; and various changes and modifications can be made as appropriate without impairing the scope of the present invention. All of the publications cited in the present specification, such as prior art documents and patent documents e.g. published patents and patent applications, are herein incorporated by reference. In the following description, the structures of the general formulas [1] to [6] are as defined above.

In the present invention, the α-fluoroaldehyde of the general formula [3] is produced by reaction of the α-fluoroester of the general formula [1] with hydrogen gas (H$_2$) in the presence of the ruthenium complex of the general formula [2].

In the α-fluoroester of the general formula [1], $R^1$ represents a halogen atom or a haloalkyl group. Examples of the halogen atom are fluorine, chlorine, bromine and iodine. Examples of the haloalkyl group are those obtained by substitution of any number of and any combination of the above halogen atoms onto any of carbon atoms of alkyl groups having 1 to 18 carbon atoms in the form of a straight-chain structure, a branched structure or a cyclic structure (in the case of 3 or more carbons). Among others, preferred is a fluorine atom.

In the α-fluoroester of the general formula [1], $R^2$ represents an alkyl group or a substituted alkyl group. Examples of the alkyl group are those having 1 to 18 carbon atoms in the form of a straight-chain structure, a branched structure or a cyclic structure (in the case of 3 or more carbons). Examples of the substituted alkyl group are those obtained by substitution of any number of and any combination of substituents onto any of carbon or nitrogen atoms of the above alkyl groups. As such substituents, there can be used: halogen atoms such as fluorine, chlorine and bromine; lower alkyl groups such as methyl, ethyl and propyl; lower haloalkyl groups such as fluoromethyl, chloromethyl and bromomethyl; lower alkoxy groups such as methoxy, ethoxy and propoxy; lower haloalkoxy groups such as fluoromethoxy, chloromethoxy and bromomethoxy; cyano group; lower alkoxycarbonyl groups such as methoxycarbonylmethyl, ethoxycarbonylethyl and propoxycarbonylpropyl; aromatic-ring groups such as phenyl, naphthyl, anthryl, pyrrolyl (including nitrogen-protected form), pyridyl, furyl, thienyl, indolyl (including nitrogen-protected form), quinolyl, benzofuryl and benzothienyl; carboxyl group; protected carboxyl groups; amino group; protected amino groups; hydroxyl group; and protected hydroxyl groups. In the substituted alkyl group, an arbitrary carbon-carbon single bond or bonds may be replaced by any number of and any combination of carbon-carbon double bonds and carbon-carbon triple bonds. (As a matter of course, the alkyl group with such an unsaturated bond or bonds may have any of the above substituent groups.) Depending on the kind of the substituent group, the substituent group itself may be involved in a side reaction. However, the side reaction can be minimized by the adoption of suitable reaction conditions. In the present specification, the term "lower" means that the group to which the term is attached is a group having 1 to 6 carbon atoms in the form of a straight-chain structure, a branched structure or a cyclic structure (in the case of 3 or more carbons). The aromatic ring groups described above as "such substituent groups" may further be substituted with a halogen atom, a lower alkyl group, a lower haloalkyl group, a lower alkoxy group, a lower haloalkoxy group, a cyano group, a lower alkoxycarbonyl group, a carboxyl group, a protected carboxyl group, an amino group, a protected amino group, a hydroxyl group, a protected hydroxyl group etc. As the protecting groups of the pyrrolyl, indolyl, carboxyl, amino and hydroxyl groups, there can be used those described in "Protective Groups in Organic Synthesis", Third Edition, 1999, John Wiley & Sons, Inc.

Among the α-fluoroester of the general formula [1], the α-fluoroester of the general formula [5] is preferred because it is easily available on a large scale. In this case, the resulting α-fluoroaldehyde of the general formula [6] is important as an intermediate for pharmaceutical and agrichemical products.

In the ruthenium complex of the general formula [2], R each independently represent a hydrogen atom, an alkyl group, a substituted alkyl group, an aromatic ring group or a substituted aromatic ring group. Examples of the alkyl and substituted alkyl groups as R are the same as those of $R^2$ in the α-fluoroester of the general formula [1]. Examples of the aromatic ring group are those having 1 to 18 carbon atoms, such as: aromatic hydrocarbon groups as typified by phenyl, naphthyl and anthryl; and aromatic heterocyclic groups containing heteroatoms e.g. as nitrogen, oxygen or sulfur as typified by pyrrolyl (including nitrogen-protected form), pyridyl, furyl, thienyl, indolyl (including nitrogen-protected form), quinolyl, benzofuryl and benzothienyl. Examples of the substituted aromatic ring group are those obtained by substitution of any number of and any combination of substituents onto any of carbon or nitrogen atoms of the above aromatic ring groups. As such substituents, there can be used the same substituents as mentioned above. Two vicinal R (except hydrogen atoms) may form a cyclic structure by covalent bond of carbon atoms with or without a nitrogen atom, an oxygen atom or a sulfur atom. In particular, it is preferable that all of eight R are hydrogen (in the case where each of two n is 1).

Ar each independently represent an aromatic ring group or a substituted aromatic ring group in the ruthenium complex of the general formula [2]. Examples of the aromatic ring and substituted aromatic ring groups as Ar are the same as those of R in the ruthenium complex of the general formula [2]. In particular, it is preferable that all of four Ar are phenyl.

X each independently represent a ligand having a formal charge of −1 or 0 with the proviso that the sum of the formal charges of three X is −2 (the formal charge of Ru is +2) in the ruthenium complex of the general formula [2]. Examples of the ligand having a formal charge of −1 or 0 are: ligands described in "Hegedus: Transition Metals in the Synthesis of Complex Organic Molecules (written by L. S. Hegedus, Second Edition, translated by Shinji Murai, p. 4-9, Tokyo Kagaku Dojin, 2001)" and in "Organic Chemistry for Graduate Students Vol. II: Molecular Structure & Reaction/Organic Metal Chemistry (Ryoji Noyori et al., p. 389-390, Tokyo Kagaku Dojin, 1999)" etc.; $BH_4^-$; and $R^4CO_2^-$. (Herein, $R^4$ represents a hydrogen atom, an alkyl group or a substituted alkyl group. Examples of the alkyl and substituted alkyl groups as $R^4$ are the same as those of $R^2$ in the α-fluoroester of the general formula [1].) In particular, it is preferable that the three ligands are hydrogen, chlorine and carbon monoxide, respectively.

The reaction can be performed in the absence of the base in the case where at least one of three X ligands is $BH_4$ in the ruthenium complex of the general formula [2]. (As a matter of course, it is alternatively feasible to perform the reaction in the presence of the base). Among others, it is preferable to use the ruthenium complex of the general formula [4] in which the Cl ligand has been replaced by $BH_4(H—BH_3)$ (see International Application Publication No. 2011/048727).

Further, n each independently represent an integer of 1 or 2 in the ruthenium complex of the general formula [2]. In the case where n is 1, a nitrogen atom and a phosphorus atom are bonded to each other via two carbon atoms in the ruthenium complex. In the case where n is 2, a nitrogen atom and a phosphorus atom are bonded to each other via three carbon atoms in the ruthenium complex. It is preferable that each of two n is 2.

In the ruthenium complex of the general formula [4], Ph represents a phenyl group.

Among the ruthenium complex of the general formula [2], the ruthenium complex of the general formula [4] is preferred. There can be used, as the ruthenium complex of the general formula [4], a commercially available complex Ru-MACHO™ (manufactured by Takasago International Corporation).

The ruthenium complex of the general formula [2] can be prepared in a similar manner with reference to the preparation process of the above complex Ru-MACHO™. Further, the ruthenium complex of the general formula [2] can be used even when water or organic solvent such as toluene is contained in the ruthenium complex. It suffices that the purity of the ruthenium complex is 70% or higher. The purity of the ruthenium complex is preferably 80% or higher, more preferably 90% or higher.

It suffices to use the ruthenium complex of the general formula [2] in an amount of 0.000001 mol or more per 1 mol of the α-fluoroester of the general formula [1]. The amount of the ruthenium complex of the general formula [2] is preferably 0.00001 to 0.005 mol, more preferably 0.00002 to 0.002 mol, per 1 mol of the α-fluoroester of the general formula [1].

Examples of the base usable in the reaction are: alkali metal hydrogencarbonates such as lithium hydrogencarbonate, sodium hydrogencarbonate and potassium hydrogencarbonate; alkali metal carbonates such as lithium carbonate, sodium carbonate and potassium carbonate; alkali metal hydroxides such as lithium hydroxide, sodium hydroxide and potassium hydroxide; tetraalkyl ammonium hydroxides such as tetramethyl ammonium hydroxide, tetraethyl ammonium hydroxide, tetra-n-propyl ammonium hydroxide and tetra-n-butyl ammonium hydroxide; alkali metal alkoxides such as lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide and potassium tert-butoxide; organic bases such as triethylamine, diisopropylethylamine, 4-dimethylaminopyridine and 1,8-diazabicyclo[5.4.0]undec-7-ene; alkali metal bis(trialkylsilyl)amides such as lithium bis(trialkylsilyl)amide, sodium bis(trialkylsilyl)amide and potassium bis(trialkylsilyl)amide; and alkali metal borohydrides such as lithium borohydride, sodium borohydride and potassium borohydrode. Among others, alkali metal alkoxides are preferred. Particularly preferred are lithium methoxide, sodium methoxide and potassium methoxide.

It suffices to use the base in an amount of 0.001 mol or more per 1 mol of the α-fluoroester of the general formula [1]. The amount of the base is preferably 0.005 to 5 mol, more preferably 0.01 to 3 mol, per 1 mol of the α-fluoroester of the general formula [1].

As it is assumed that the true catalytic active species is derived from the ruthenium catalyst of the general formula [2] optionally in the presence of the base, the case where the catalytic active species (including isolated form) is prepared in advance and used in the reduction reaction is included in the scope of the present invention.

It suffices to use the hydrogen gas in an amount of 1 mol or more per 1 mol of the α-fluoroester of the general formula [1]. The hydrogen gas is preferably used in a large excessive amount, more preferably in a large excessive amount under the following pressurized conditions.

There is no particular limitation on the hydrogen pressure. The hydrogen pressure is preferably 2 to 0.001 MPa, more preferably 1 to 0.01 MPa. It is particularly preferred that the hydrogen pressure is 0.05 MPa or lower in order to maximize the effects of the present invention.

Examples of the reaction solvent usable in the reaction are: aliphatic hydrocarbon solvents such as n-hexane and n-heptane; aromatic hydrocarbon solvents such as toluene and xylene; halogenated solvents such as methylene chloride and 1,2-dichloroethane; ether solvents such as diethyl ether, 1,2-dimethoxyethane, 1,4-dioxane, tetrahydrofuran, 2-methyltetrahydrofuran, tert-butyl methyl ether, diisopropyl ether, diethylene glycol dimethyl ether and anisole; alcohol solvents such as methanol, ethanol, n-propanol, isopropanol, n-butanol, tert-butanol, n-pentanol, n-hexanol and cyclohexanol; amide solvents such as N,N-dimethylformamide and 1,3-dimethyl-2-imidazolidinone; nitrile solvents such as acetonitrile and propionitrile; dimethyl sulfoxide; and water. Among others, ether solvents and alcohol solvents are preferred. Alcohol solvents are more preferred as the reaction solvent. These reaction solvents can be used solely or in combination of two or more thereof. It is particularly preferable to use methanol, ethanol or propanol, each of which is easy to separate by fractional distillation, for production of the α-fluoroaldehyde of the general formula [6] (or the aftermentioned synthetic equivalent thereof) as the preferred target compound.

It suffices to use the reaction solvent in an amount of 0.01 L (liter) or more per 1 mol of the α-fluoroester of the general formula [1]. The amount of the reaction solvent is preferably 0.03 to 10 L, more preferably 0.05 to 7 L, per 1 mol of the α-fluoroester of the general formula [1]. The reaction can alternatively be performed under neat conditions without the use of the reaction solvent.

It suffices that the reaction temperature is +150° C. or lower. The reaction temperature is preferably +125 to −50° C., more preferably +100 to −25° C.

Further, it suffices that the reaction time is 72 hours or less. As the reaction time varies depending on the raw substrate material and reaction conditions, it is preferable to determine the time at which there is seen almost no decrease of the raw substrate material as the end of the reaction while monitoring the progress of the reaction by any analytical means such as gas chromatography, liquid chromatography or nuclear magnetic resonance.

The α-fluoroaldehyde of the general formula [3] can be obtained by any ordinary post treatment operation for organic synthesis.

As the α-fluoroaldehyde of the general formula [3] is an aldehyde having directly bonded thereto a strong electron-attracting group, it is often the case that the α-fluoroaldehyde of the general formula [3] is obtained as stable synthetic equivalents such as a self-polymerization product, hydrate and hemiacetal. (As a matter of course, the α-fluoroaldehyde of the general formula [3] can be obtained in the form of an aldehyde.) These synthetic equivalents are thus included in the α-fluoroaldehyde of the general formula [3] as the scope of the present invention. (The same applies to that of the general formula [6].) Herein, the alcohol function of the hemiacetal is derived from the alkali metal alkoxide used as the base, the alcohol used as the reaction solvent (see Example 6), the ester moiety of the raw material substrate (i.e. $OR^2$ in the α-fluoroester of the general formula [1]) or the like. It is feasible to replace the alcohol function of the hemiacetal with an arbitrary alcohol function by shifting the equilibrium of the reaction system upon the addition of the arbitrary alcohol during post treatment (see Example 8). (The "arbitrary alcohol function" refers to those having 1 to 18 carbon atoms in the form of a straight-chain structure, a branched structure or a cyclic structure (in the case of 3 or more carbons).) Similarly, the hydrate can be obtained upon the addition of water.

Further, the crude product can be purified to a high purity, as needed, by activated carbon treatment, fractional distillation, recrystallization, column chromatography or the like. It is convenient to recover the target compound by directly subjecting the reaction completed solution to recovery distillation in the case where the target compound has a low boiling point. In the case where the reaction is performed in the presence of the base, the relatively highly acidic target compound (such as self-polymerization product, hydrate, hemicacetal etc.) tends to form a salt or complex with the base and remain in the residue of distillation. In such a case, it is feasible to obtain the target compound with high yield by neutralizing the reaction completed solution with an organic acid such as formic acid, acetic acid, citric acid, oxalic acid, benzoic acid, methanesulfonic acid or paratoluenesulfonic acid or an inorganic acid such as hydrogen chloride, hydrogen bromide, nitric acid or sulfuric acid in advance, and then, subjecting the neutralized reaction completed solution to recovery distillation (including recovery by washing the distillation residue with an organic solvent such as diisopropyl ether).

EXAMPLES

The present invention will be described in more detail below by way of the following examples. It should be noted that the following examples are illustrative and are not intended to limit the present invention thereto. In the following description, the abbreviations "Me", "Ph", and "Et" refer to methyl, phenyl and ethyl, respectively.

Example 1

A pressure-proof reaction vessel of stainless steel (SUS) was charged with 2.6 g (20 mmol, 1 eq) of α-fluoroester of the following formula, 6.1 mg (purity: 94.2%; 9.5 μmol, 0.0005 eq) of ruthenium complex of the following formula, 270 mg (5.0 mmol, 0.25 eq) of sodium methoxide and 10 mL (0.5 L/mol) of methanol.

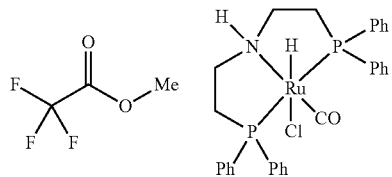

The inside of the reaction vessel was replaced five times with hydrogen gas. The hydrogen pressure inside the reaction vessel was then set to 1.0 MPa. The resulting solution inside the reaction vessel was stirred all night at 35° C. It was confirmed by $^{19}$F-NMR analysis of the reaction completed solution that the conversion rate of the reaction and the selectivity of α-fluoroaldehyde equivalent of the following formula were 96% and 62.3%, respectively.

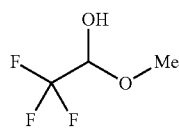

It was also confirmed that the selectivity of β-fluoroalcohol of the following formula as an excessive reduction product was 37.7%.

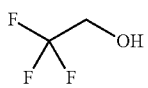

The $^{1}$H- and $^{19}$F-NMR data and gas chromatographic data of the obtained α-fluoroaldehyde equivalent was in agreement with those of the reference standard. For reference purposes, the reaction procedure and reaction results of the present example are summarized in the following scheme.

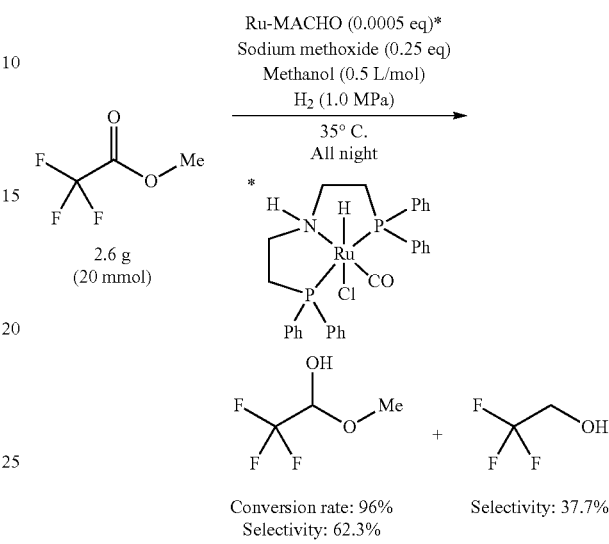

Example 2

A pressure-proof reaction vessel of stainless steel (SUS) was charged with 2.6 g (20 mmol, 1 eq) of α-fluoroester of the following formula, 6.1 mg (purity: 94.2%; 9.5 μmol, 0.0005 eq) of ruthenium complex of the following formula, 270 mg (5.0 mmol, 0.25 eq) of sodium methoxide and 10 mL (0.5 L/mol) of methanol.

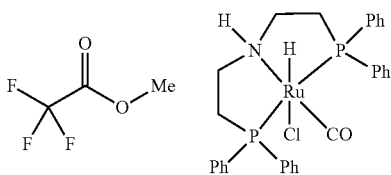

The inside of the reaction vessel was replaced five times with hydrogen gas. The hydrogen pressure inside the reaction vessel was then set to 0.5 MPa. The resulting solution inside the reaction vessel was stirred all night at 35° C. It was confirmed by $^{19}$F-NMR analysis of the reaction completed solution that the conversion rate of the reaction and the selectivity of α-fluoroaldehyde equivalent of the following formula were 97% and 72.4%, respectively.

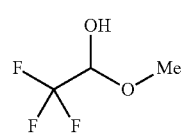

It was also confirmed that the selectivity of β-fluoroalcohol of the following formula as an excessive reduction product was 27.6%.

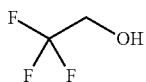

The ¹H- and ¹⁹F-NMR data and gas chromatographic data of the obtained α-fluoroaldehyde equivalent was in agreement with those of the reference standard. For reference purposes, the reaction procedure and reaction results of the present example are summarized in the following scheme.

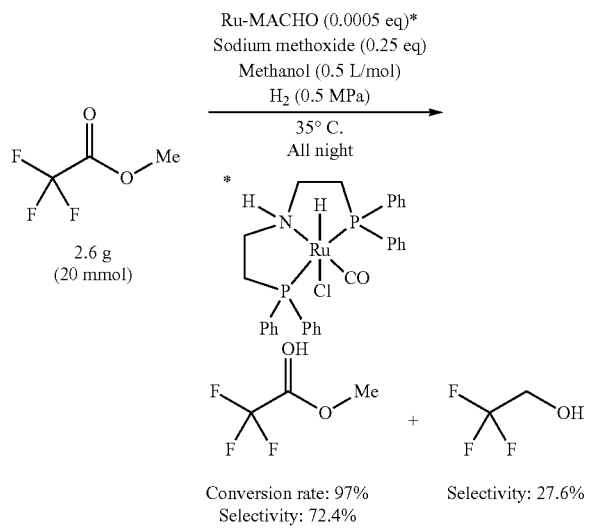

Conversion rate: 97%  Selectivity: 27.6%
Selectivity: 72.4%

Example 3

A pressure-proof reaction vessel of stainless steel (SUS) was charged with 5.8 g (40 mmol, 1 eq) of α-fluoroester of the following formula, 13 mg (purity: 94.2%; 20 μmol, 0.0005 eq) of ruthenium complex of the following formula, 540 mg (10.0 mmol, 0.25 eq) of sodium methoxide and 20 mL (0.5 L/mol) of methanol.

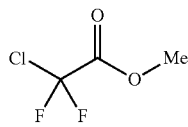

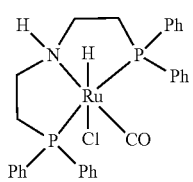

The inside of the reaction vessel was replaced five times with hydrogen gas. The hydrogen pressure inside the reaction vessel was then set to 1.0 MPa. The resulting solution inside the reaction vessel was stirred all night at 35° C. It was confirmed by ¹⁹F-NMR analysis of the reaction completed solution that the conversion rate of the reaction and the selectivity of α-fluoroaldehyde equivalent of the following formula were 83% and 89.4%, respectively.

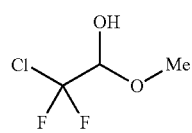

It was also confirmed that the selectivity of β-fluoroalcohol of the following formula as an excessive reduction product was 10.6%.

The ¹H- and ¹⁹F-NMR data and gas chromatographic data of the obtained α-fluoroaldehyde equivalent was in agreement with those of the reference standard. For reference purposes, the reaction procedure and reaction results of the present example are summarized in the following scheme.

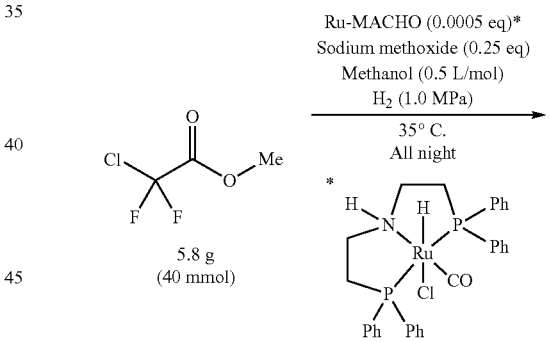

Conversion rate: 83%  Selectivity: 10.6%
Selectivity: 89.4%

Example 4

A pressure-proof reaction vessel of stainless steel (SUS) was charged with 14 g (100 mmol, 1 eq) of α-fluoroester of the following formula, 6.4 mg (purity: 94.2%; 10 μmol, 0.0001 eq) of ruthenium complex of the following formula, 840 mg (10.0 mmol, 0.1 eq) of potassium ethoxide and 44 mL (0.4 L/mol) of ethanol.

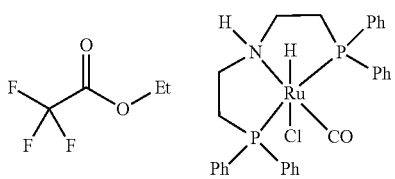

The inside of the reaction vessel was replaced five times with hydrogen gas. The hydrogen pressure inside the reaction vessel was then set to 0.8 MPa. The resulting solution inside the reaction vessel was stirred all night at 38° C. It was confirmed by $^{19}$F-NMR analysis of the reaction completed solution that the conversion rate of the reaction and the selectivity of α-fluoroaldehyde equivalent of the following formula were 91% and 83.0%, respectively.

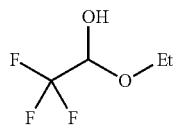

It was also confirmed that the selectivity of β-fluoroalcohol of the following formula as an excessive reduction product was 17.0%.

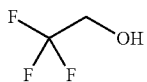

The $^1$H- and $^{19}$F-NMR data and gas chromatographic data of the obtained α-fluoroaldehyde equivalent was in agreement with those of the reference standard. For reference purposes, the reaction procedure and reaction results of the present example are summarized in the following scheme.

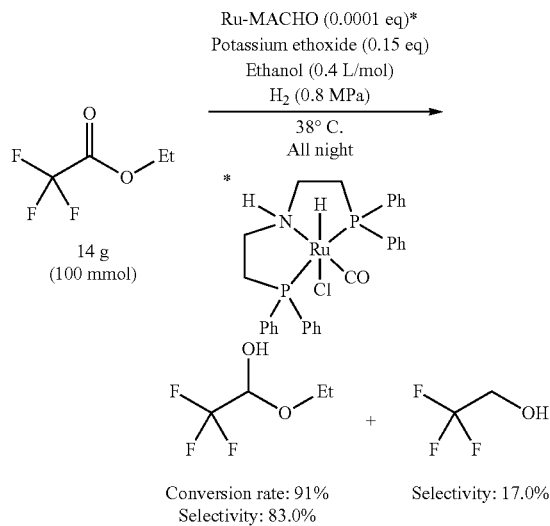

Example 5

A pressure-proof reaction vessel of stainless steel (SUS) was charged with 8.9 g (50 mmol, 1 eq) of α-fluoroester of the following formula, 6.4 mg (purity: 94.2%; 10 μmol, 0.0002 eq) of ruthenium complex of the following formula, 270 mg (5.0 mmol, 0.1 eq) of sodium methoxide and 25 mL (0.5 L/mol) of methanol.

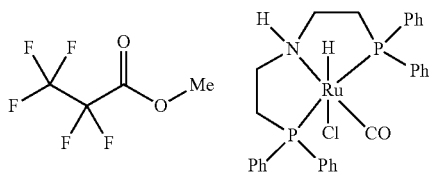

The inside of the reaction vessel was replaced five times with hydrogen gas. The hydrogen pressure inside the reaction vessel was then set to 0.5 MPa. The resulting solution inside the reaction vessel was stirred all night at 35° C. It was confirmed by $^{19}$F-NMR analysis of the reaction completed solution that the conversion rate of the reaction and the selectivity of α-fluoroaldehyde equivalent of the following formula were 84% and 80.0%, respectively.

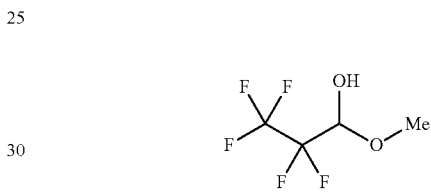

It was also confirmed that the selectivity of β-fluoroalcohol of the following formula as an excessive reduction product was 20.0%.

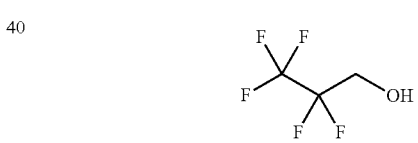

The $^1$H- and $^{19}$F-NMR data and gas chromatographic data of the obtained α-fluoroaldehyde equivalent was in agreement with those of the reference standard. For reference purposes, the reaction procedure and reaction results of the present example are summarized in the following scheme.

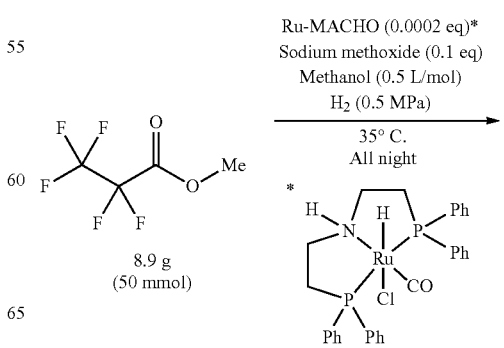

-continued

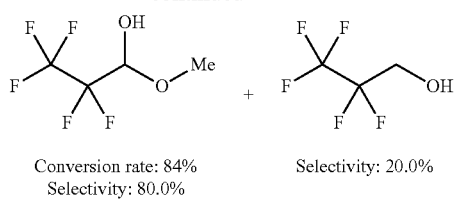

Conversion rate: 84%
Selectivity: 80.0%

Selectivity: 20.0%

Example 6

A pressure-proof reaction vessel of stainless steel (SUS) was charged with 61 g (480 mmol, 1 eq) of α-fluoroester of the following formula, 62 mg (purity: 94.2%; 96 μmol, 0.0002 eq) of ruthenium complex of the following formula, 3.3 g (48 mmol, 0.1 eq) of sodium ethoxide and 220 mL (0.5 L/mol) of ethanol.

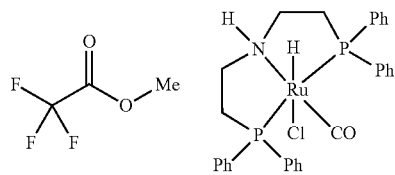

The inside of the reaction vessel was replaced five times with hydrogen gas. The hydrogen pressure inside the reaction vessel was then set to 0.9 MPa. The resulting solution inside the reaction vessel was stirred all night at 38° C. It was confirmed by $^{19}$F-NMR analysis of the reaction completed solution that the conversion rate of the reaction, the selectivity of α-fluoroaldehyde equivalent (ethyl hemiacetal) of the following formula and the selectivity of α-fluoroaldehyde equivalent (methyl hemiacetal) of the following formula were 95%, 60.9% and 7.9%, respectively.

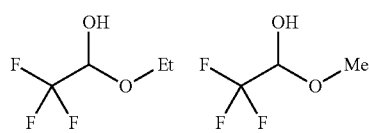

It was also confirmed that the selectivity of β-fluoroalcohol of the following formula as an excessive reduction product was 31.2%.

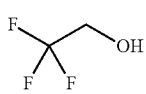

The $^1$H- and $^{19}$F-NMR data and gas chromatographic data of the obtained α-fluoroaldehyde equivalents (ethyl hemiacetal and methyl hemiacetal) was in agreement with those of the reference standards. For reference purposes, the reaction procedure and reaction results of the present example are summarized in the following scheme.

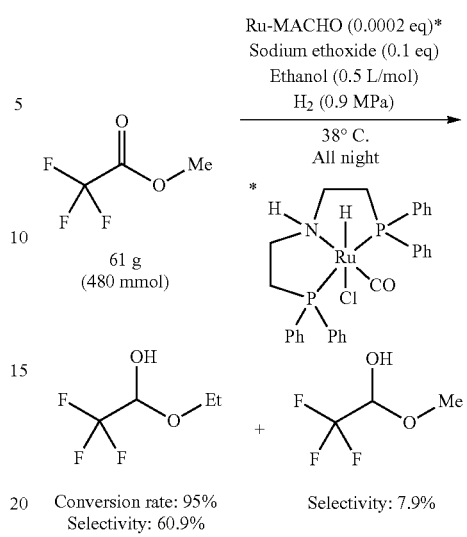

Conversion rate: 95%
Selectivity: 60.9%

Selectivity: 7.9%

Selectivity: 31.2%

Example 7

A pressure-proof reaction vessel of stainless steel (SUS) was charged with 130 g (1.0 mol, 1 eq) of α-fluoroester of the following formula, 32 mg (purity: 94.2%; 50 μmol, 0.00005 eq) of ruthenium complex of the following formula, 11 g (200 mmol, 0.2 eq) of sodium methoxide and 500 mL (0.5 L/mol) of methanol.

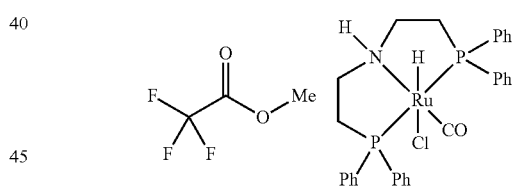

The inside of the reaction vessel was replaced five times with hydrogen gas. The hydrogen pressure inside the reaction vessel was then set to 0.9 MPa. The resulting solution inside the reaction vessel was stirred all night at 35° C. It was confirmed by $^{19}$F-NMR analysis of the reaction completed solution that the conversion rate of the reaction and the selectivity of α-fluoroaldehyde equivalent of the following formula were 89% and 96.0%, respectively.

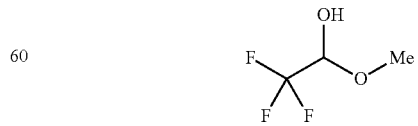

It was also confirmed that the selectivity of β-fluoroalcohol of the following formula as an excessive reduction product was 4.0%.

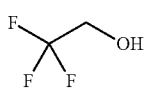

The $^1$H- and $^{19}$F-NMR data and gas chromatographic data of the obtained α-fluoroaldehyde equivalent was in agreement with those of the reference standard. For reference purposes, the reaction procedure and reaction results of the present example are summarized in the following scheme.

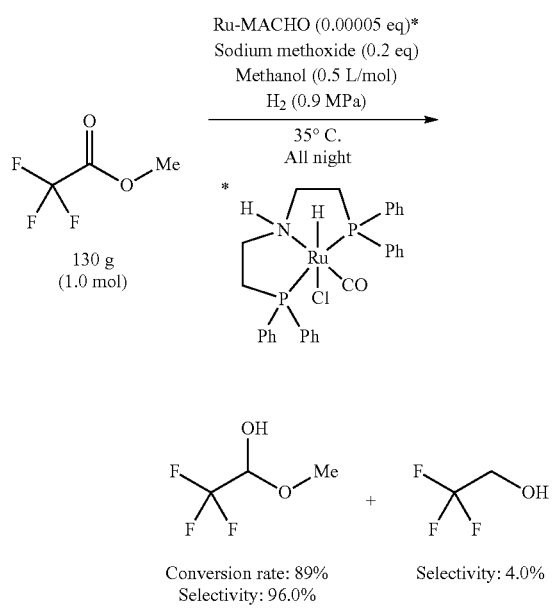

To the reaction completed solution, 4.5 g (75 mmol, 0.075 eq) of acetic acid was added. The resulting solution was directly subjected to recovery distillation (oil bath temperature: ~63° C., vacuum degree: ~1.6 kPa) so that the target compound was recovered in the form of a methanol solution thereof. The methanol solution was then subjected to fractional distillation (theoretical plate number: 20, distillation temperature: 93° C., atmospheric pressure). By this, 93 g of α-fluoroaldehyde equivalent of the above formula was obtained. The yield of α-fluoroaldehyde equivalent was 67% as determined by internal standard method (internal standard material: α,α,α-trifluorotoluene, quantitative value: 87 g). The $^{19}$F-NMR purity of α-fluoroaldehyde equivalent was 98.0% or higher. The contents of methanol content and water were 7.0% or lower and 0.05% or lower, respectively.

Example 8

A pressure-proof reaction vessel of stainless steel (SUS) was charged with 154 g (1.2 mol, 1 eq) of α-fluoroester of the following formula, 150 mg (purity: 94.2%; 240 μmol, 0.0002 eq) of ruthenium complex of the following formula, 6.5 g (120 mmol, 0.1 eq) of sodium methoxide and 530 mL (0.4 L/mol) of methanol.

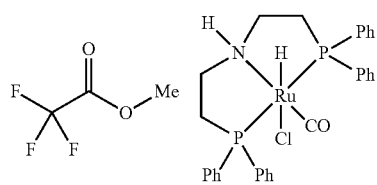

The inside of the reaction vessel was replaced five times with hydrogen gas. The hydrogen pressure inside the reaction vessel was then set to 0.9 MPa. The resulting solution inside the reaction vessel was stirred for 8 hours at 38° C. It was confirmed by $^{19}$F-NMR analysis of the reaction completed solution that the conversion rate of the reaction and the selectivity of α-fluoroaldehyde equivalent (methyl hemiacetal) of the following formula were 92% and 91.2%, respectively.

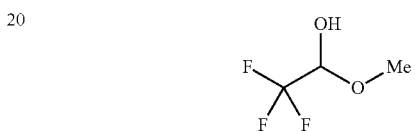

It was also confirmed that the selectivity of β-fluoroalcohol of the following formula as an excessive reduction product was 8.8%.

The $^1$H- and $^{19}$F-NMR data and gas chromatographic data of the obtained α-fluoroaldehyde equivalent was in agreement with those of the reference standard. For reference purposes, the reaction procedure and reaction results of the present example are summarized in the following scheme.

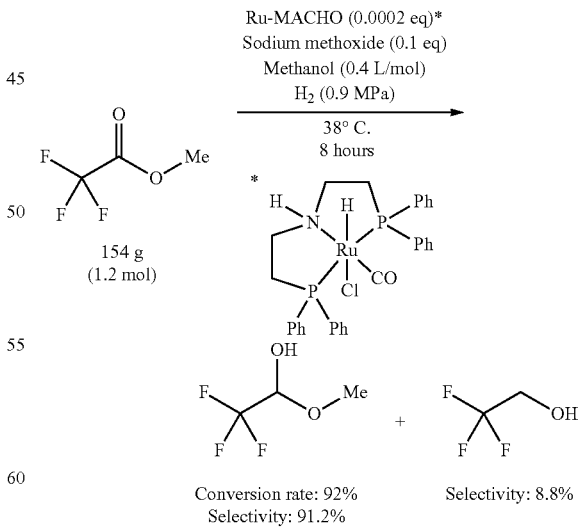

To the reaction completed solution, 6.5 g (110 mmol, 0.09 eq) of acetic acid was added. The resulting solution was directly subjected to recovery distillation (oil bath temperature: ~80° C., vacuum degree: ~1.8 kPa) so that the target compound was recovered in the form of a methanol solution thereof. The methanol solution was then subjected to fractional distillation (theoretical plate number: 10, distillation temperature: 106° C., atmospheric pressure). (The distillation was continued with the addition of 120 g (2.6 mol, 2.2 eq) of ethanol to the distillation still (i.e. the distillation residue containing the target compound) at the time the major portion of methanol was distilled.) By this, 97 g of α-fluoroaldehyde equivalent (ethyl hemiacetal) of the following formula was obtained.

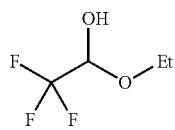

The contents of methanol, ethanol, α-fluoroaldehyde equivalent (methyl hemiacetal) of the above formula and α-fluoroaldehyde equivalent (ethyl hemiacetal) of the above formula were determined by gas chromatographic analysis to be <0.1%, 14.8%, 0.1% and 84.5%, respectively. The yield of α-fluoroaldehyde equivalent (ethyl hemiacetal) was 48% in view of the gas chromatographic purity.

Example 9

A pressure-proof reaction vessel of stainless steel (SUS) was charged with 1.6 g (10 mmol, 1 eq) of α-fluoroester of the following formula, 0.9 mg (purity: 94.2%; 1.4 μmol, 0.00014 eq) of ruthenium complex of the following formula, 54 mg (1.0 mmol, 0.10 eq) of sodium methoxide and 10 mL (1.0 L/mol) of methanol.

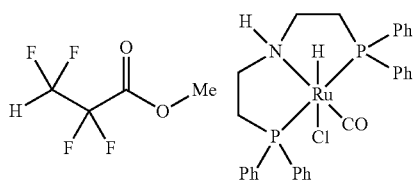

The inside of the reaction vessel was replaced five times with hydrogen gas. The hydrogen pressure inside the reaction vessel was then set to 0.5 MPa. The resulting solution inside the reaction vessel was stirred all night at 36° C. It was confirmed by $^{19}$F-NMR analysis of the reaction completed solution that the conversion rate of the reaction and the selectivity of α-fluoroaldehyde equivalent of the following formula were 24% and 90.0%, respectively.

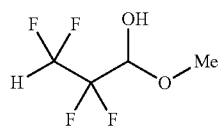

It was also confirmed that the selectivity of β-fluoroalcohol of the following formula as an excessive reduction product was 10.0%.

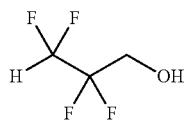

The $^1$H- and $^{19}$F-NMR data and gas chromatographic data of the obtained α-fluoroaldehyde equivalent was in agreement with those of the reference standard. For reference purposes, the reaction procedure and reaction results of the present example are summarized in the following scheme.

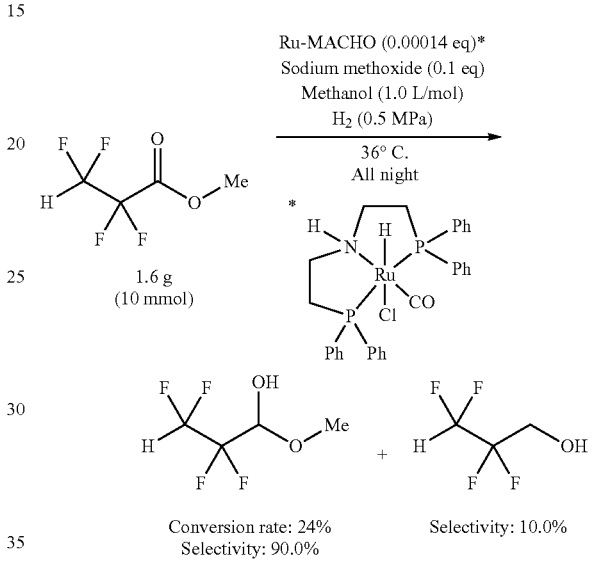

Comparative Example 1

A pressure-proof reaction vessel of stainless steel (SUS) was charged with 53 g (480 mmol, 1 eq) of α-fluoroester of the following formula, 15 mg (purity: 94.2%; 24 μmol, 0.00005 eq) of ruthenium complex of the following formula, 8.4 g (120 mmol, 0.25 eq) of potassium methoxide and 240 mL (0.5 L/mol) of methanol.

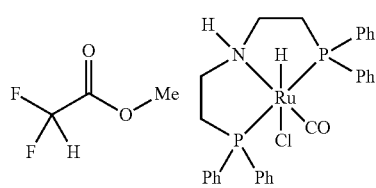

The inside of the reaction vessel was replaced five times with hydrogen gas. The hydrogen pressure inside the reaction vessel was then set to 1.0 MPa. The resulting solution inside the reaction vessel was stirred all night at 40° C. It was confirmed by gas chromatographic analysis of the reaction completed solution that the conversion rate of the reaction and the selectivity of β-fluoroalcohol of the following formula were 100% and 97.6%, respectively.

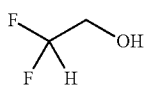

For reference purposes, the reaction procedure and reaction results of the present example are indicated in the following scheme.

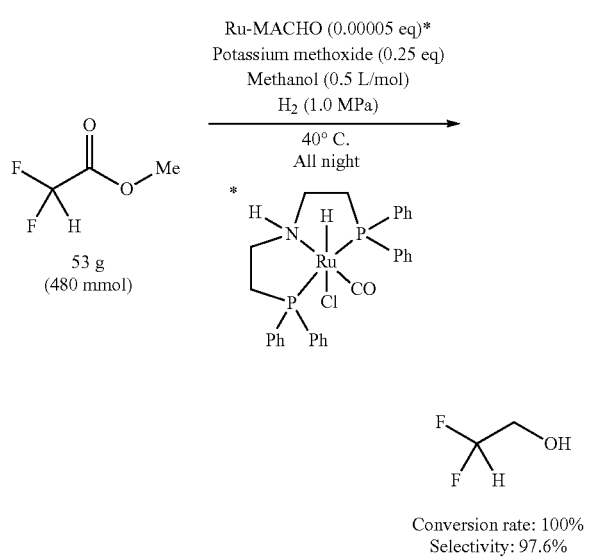

Conversion rate: 100%
Selectivity: 97.6%

The above reaction operation was repeated five times to obtain the reaction completed solution equivalent to 2.4 mol of α-fluoroester. Then, 36 g (600 mmol, 0.25 eq) of acetic acid was added to the reaction completed solution. The resulting solution was directly subjected to recovery distillation (oil bath temperature: 55° C., vacuum degree: ~1.5 kPa) so that the target compound was recovered in the form of a methanol solution thereof. The distillation residue (i.e. the solid matter containing the target compound and potassium acetate) was washed by stirring with 200 mL of diisopropyl ether and filtered out. The thus-obtained solid matter was further washed with 200 mL of diisopropyl ether. In each of these washing operations, the target compound was recovered in the form of a diisopropyl ether solution thereof. The recovered solutions were combined and subjected to fractional distillation (theoretical plate number: 20, distillation temperature: 92° C., atmospheric pressure). By this, 158 g of β-fluoroalcohol of the above formula was obtained. The yield of β-fluoroalcohol was 80%. The gas chromatographic purity of β-fluoroalcohol was 99.6%. The content of water was 0.05%.

Comparative Example 2

A pressure-proof reaction vessel of stainless steel (SUS) was charged with 5.0 g (40 mmol, 1 eq) of α-fluoroester of the following formula, 10 mg (purity: 94.2%; 16 μmol, 0.0004 eq) of ruthenium complex of the following formula, 700 mg (10 mmol, 0.25 eq) of potassium methoxide and 20 mL (0.5 L/mol) of methanol.

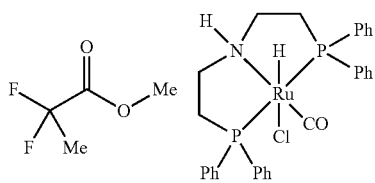

The inside of the reaction vessel was replaced five times with hydrogen gas. The hydrogen pressure inside the reaction vessel was then set to 1.0 MPa. The resulting solution inside the reaction vessel was stirred all night at 37° C. It was confirmed by gas chromatographic analysis of the reaction completed solution that the conversion rate of the reaction and the selectivity of β-fluoroalcohol of the following formula were 92% and 98.9%, respectively.

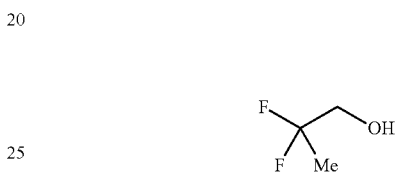

The reaction procedure and reaction results of the present example are indicated in the following scheme for reference purposes.

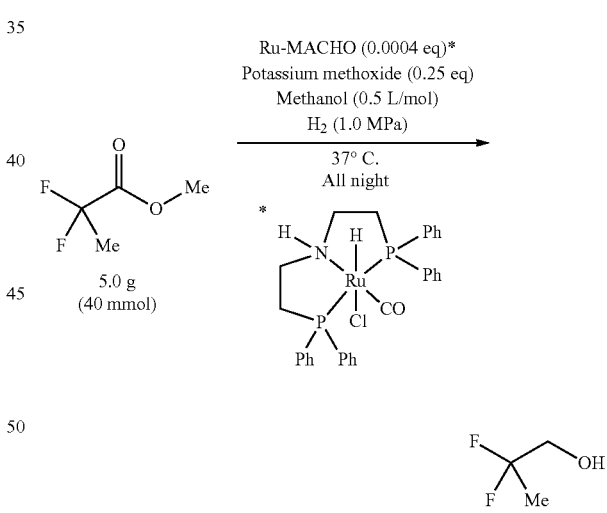

Conversion rate: 92%
Selectivity: 98.9%

Comparative Example 3

A pressure-proof reaction vessel of stainless steel (SUS) was charged with 4.0 g (20 mmol, 1 eq) of α-fluoroester of the following formula, 4.3 mg (purity: 94.2%; 6.7 μmol, 0.0003 eq) of ruthenium complex of the following formula, 270 mg (5.0 mmol, 0.25 eq) of sodium methoxide and 10 mL (0.5 L/mol) of methanol.

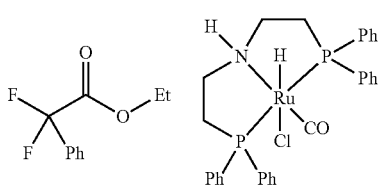

The inside of the reaction vessel was replaced five times with hydrogen gas. The hydrogen pressure inside the reaction vessel was then set to 1.0 MPa. The resulting solution inside the reaction vessel was stirred all night at 40° C. It was confirmed by gas chromatographic analysis of the reaction completed solution that the conversion rate of the reaction and the selectivity of β-fluoroalcohol of the following formula were 100% and 98.2%, respectively.

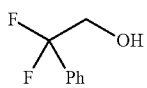

The reaction procedure and reaction results of the present example are indicated in the following scheme for reference purposes.

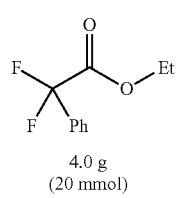
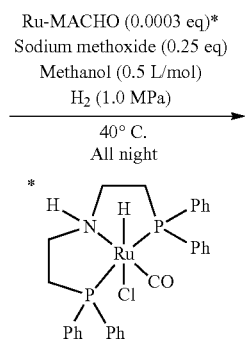
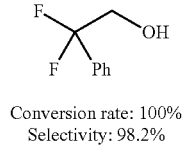

Conversion rate: 100%
Selectivity: 98.2%

Comparative Example 4

A pressure-proof reaction vessel of stainless steel (SUS) was charged with 38 g (250 mmol, 1 eq) of α-fluoroester of the following formula, 64 mg (purity: 94.2%; 100 μmol, 0.0004 eq) of ruthenium complex of the following formula, 3.4 g (63 mmol, 0.25 eq) of sodium methoxide and 250 mL (1.0 L/mol) of methanol.

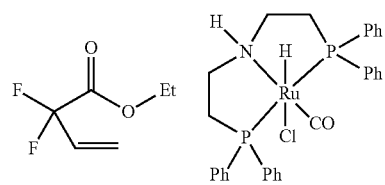

The inside of the reaction vessel was replaced five times with hydrogen gas. The hydrogen pressure inside the reaction vessel was then set to 1.0 MPa. The resulting solution inside the reaction vessel was stirred all night at 35° C. It was confirmed by $^{19}$F-NMR analysis of the reaction completed solution that the conversion rate of the reaction and the selectivity of β-fluoroalcohol of the following formula were 100% and 98.0%, respectively.

The reaction procedure and reaction results of the present example are indicated in the following scheme for reference purposes.

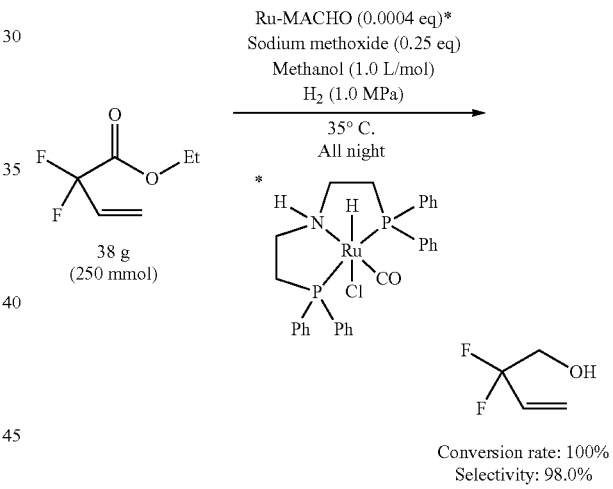

Conversion rate: 100%
Selectivity: 98.0%

The above reaction operation was repeated twice to obtain the reaction completed solution equivalent to 470 mmol of α-fluoroester. Then, 7.1 g (120 mmol, 0.25 eq) of acetic acid and an appropriate amount of methoquinone (polymerization inhibitor) were added to the reaction completed solution. The resulting solution was directly subjected to recovery distillation (oil bath temperature: ~63° C., vacuum degree: ~7.9 kPa) so that the target compound was recovered in the form of a methanol solution thereof. The distillation residue (i.e. the solid matter containing the target compound and sodium acetate) was washed by stirring with 400 mL of diisopropyl ether and filtered out. The thus-obtained solid matter was further washed with a small amount of diisopropyl ether. In each of these washing operations, the target compound was recovered in the form of a diisopropyl ether solution thereof. The recovered solutions were combined and subjected to fractional distillation (theoretical plate number: 4, distillation temperature: 57 to 62° C., 13 to 12 kPa). By this, 40 g of β-fluoroalcohol of the above formula was obtained. The yield of β-fluoroalcohol was 78%. The gas chromatographic purity of β-fluoroalcohol was 98.9%. The $^1$H- and $^{19}$F-NMR measurement results of β-fluoroalcohol are indicated below.

$^1$H-NMR (reference material: Me$_4$Si, deuterated solvent: CDCl$_3$) δ ppm; 2.21 (br, 1H), 3.81 (t, 2H), 5.55 (d, 1H), 5.74 (m, 1H), 5.97 (m, 1H).

$^{19}$F-NMR (reference material: C$_6$F$_6$, deuterated solvent: CD$_3$OD) δ ppm; 55.44 (m, 2F).

As described above, there is no need to use special production equipment for hydrogen reduction of the α-fluoroester in the present invention. There is also no need to use a high-pressure gas production facility by adoption of the preferable hydrogen pressure condition (1 MPa or lower) in the present invention. It is therefore possible to allow relatively easy industrial production of the α-fluoroaldehyde. Further, it is possible to directly obtain, as stable synthetic equivalents of the α-fluoroaldehyde, not only a hydrate (as by conventional techniques) but also a hemiacetal that is easy to purify and is of high value in synthetic applications.

Industrial Applicability

The α-fluoroaldehydes produced by the production method according to the present invention are usable as intermediates for pharmaceutical and agrichemical products.

The invention claimed is:

1. A process for producing an α-fluoroaldehyde of the general formula [3], comprising: reaction of an α-fluoroester of the general formula [1] with hydrogen gas (H$_2$) in the presence of a ruthenium complex of the general formula [2]

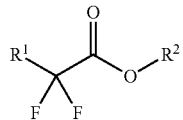

[1]

where R$^1$ represents a halogen atom or a haloalkyl group; and R$^2$ represents an alkyl group or a substituted alkyl group,

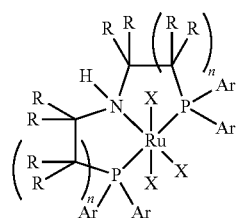

[2]

where R each independently represents a hydrogen atom, an alkyl group, a substituted alkyl group, an aromatic ring group or a substituted aromatic ring group; Ar each independently represents an aromatic ring group or a substituted aromatic ring group; X each independently represents a ligand with a formal charge of −1 or 0 (with the proviso that the sum of the formal charges of three X is −2); and n each independently represents an integer of 1 or 2,

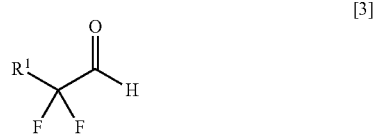

[3]

where R$^1$ has the same meaning as in the general formula [1].

2. The process according to claim 1, wherein the reaction is performed in the presence of a base.

3. The process according to claim 1, wherein the ruthenium complex of the general formula [2] is a ruthenium complex of the general formula [4]

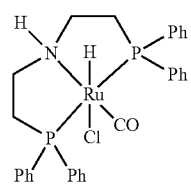

[4]

where Ph represents a phenyl group.

4. The process according to claim 1, wherein the α-fluoroester of the general formula [1] is an αfluoroester of the general formula [5]; and the α-fluoroaldehyde of the general formula [3] is an α-fluoroaldehyde of the general formula [6]

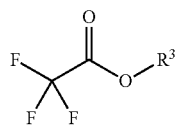

[5]

where R$^3$ is an alkyl group,

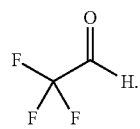

[6]

5. The process according to claim 1, wherein the reaction is performed at a hydrogen pressure of 2 MPa or lower.

6. The process according to claim 5, wherein the reaction is performed at a hydrogen pressure of 1 MPa or lower.

7. The process according to claim 6, wherein the reaction is performed at a hydrogen pressure of 0.5 MPa or lower.

* * * * *